United States Patent [19]

van der Heide

[11] Patent Number: 5,388,568
[45] Date of Patent: Feb. 14, 1995

[54] MANIPULATOR ASSEMBLY FOR AN ENDOSCOPE

[75] Inventor: Hendrik T. van der Heide, Gouda, Netherlands

[73] Assignee: B.V. Optische Industrie "De Oude Delft", Delft, Netherlands

[21] Appl. No.: 961,685

[22] PCT Filed: Jul. 8, 1991

[86] PCT No.: PCT/NL91/00121
§ 371 Date: Mar. 8, 1993
§ 102(e) Date: Mar. 8, 1993

[87] PCT Pub. No.: WO92/00696
PCT Pub. Date: Jan. 23, 1992

[30] Foreign Application Priority Data

Jul. 9, 1990 [NL] Netherlands .................. 9001564

[51] Int. Cl.[6] ............................. A61B 1/04
[52] U.S. Cl. ................................. 128/4
[58] Field of Search .................... 128/4, 6, 5, 7-11, 128/656-658; 604/95; 403/43-48; 74/479 BF; 901/21

[56] References Cited

U.S. PATENT DOCUMENTS

| | | | |
|---|---|---|---|
| 4,207,873 | 6/1980 | Kruy | 128/6 |
| 4,461,282 | 7/1984 | Ouchi et al. | 128/4 |
| 4,688,555 | 8/1987 | Wardle | 128/4 |
| 4,742,816 | 5/1988 | Suzuki et al. | 128/4 |

*Primary Examiner*—Richard J. Apley
*Assistant Examiner*—John P. Leubecker
*Attorney, Agent, or Firm*—Louis E. Marn

[57] ABSTRACT

A manipulator assembly for an endoscope includes a housing for a pair of control cables, first and second gear members disposed for rotation within the housing, and an endless toothed belt member coursed about such gear members and connected to the control cables. A control knob is provided for rotating the first gear member and a stepping assembly engages the second gear member for effecting a stepwise movement of the endless belt. The stepping assembly includes a knurled disc coupled to the second gear member and a resilient element engaging the knurled disc. A control element is provided outside of the housing for disengaging the stepping assembly. The control element includes a cam disc for disengaging the resilient element from the knurled disc.

8 Claims, 1 Drawing Sheet

MANIPULATOR ASSEMBLY FOR AN ENDOSCOPE

BACKGROUND OF THE INVENTION

1. Field of the Invention

The invention relates to a tube which can be introduced into the body through a body orifice.

2. Brief Description of the Prior Art

Such a tube, which is also known under the name of an endoscope, is known from U.S. Pat. No. 4,207,873 and is designed to permit maneuvering of the flexible end of the endoscope into any desired position relative to the body of the endoscope by means of two pairs of cables in the body of a patient. For this, each cable of a pair is fixed to a rack which is movable in the lengthwise direction of the elongated housing, while a single toothed wheel is placed between the pair of racks belonging to one pair of cables, which toothed wheel is connected to a control knob placed outside the housing. By turning this control knob and the toothed wheel with it, the racks are moved in opposite directions relative to the housing, as a result of which one cable is pulled in and the other cable paid out, so that the flexible end of the endoscope is moved in one plane. Due to the fact that provision is made for two pairs of cables each with its own pair of racks, a toothed wheel and a control knob, operation of the two control knobs permits a movement of the flexible end in two planes at right angles to each other and to all positions lying there between. In order to be able to move and fix the flexible end very accurately, the known device is provided with a mechanism fitted in the interior of each of the control knobs and having spring catches which can engage on a toothed wheel. This mechanism can be put out of action by pulling the relevant knob outwards relative to the housing.

The manipulator of the known endoscope is designed so that in virtually all cases it can be operated with one hand by the person operating it, so that the person keeps the other hand free to guide the tube of the endoscope. In practice, however, disconnecting the click mechanism of one or both control knobs with only one hand is found to be extremely difficult. Another disadvantage of the known manipulator is that it is fairly expensive, due to the fact that racks which are labour-intensive to manufacture and thus expensive are used. Besides, the toothed ring forming part of the stepwise movement mechanism is provided in the axial direction with an additional edge serving to prevent accidental movement from the disconnected state to the coupled state, and the provision of such an edge requires an additional operation and is thus expensive.

The object of the invention is therefore to provide a tube which is provided with a manipulator 5 which can be controlled without any problem with one hand also for disconnecting the stepwise movement mechanism, and which can also be manufactured considerably more cheaply than the known tube.

SUMMARY OF THE INVENTION

To this end, the invention provides a tube of the above-mentioned type in which the means provided with a toothing comprise a toothed belt which is guided over two toothed wheels, of which the first is the toothed wheel coupled to the control knob and the second is rotatable mounted inside the housing and is connected to the stepwise movement means in order to provide a stepwise movement facility of the toothed belt, said stepwise movement means being accommodated in the housing and being disconnectable by means of a separate control element placed on the outside of the housing.

The stepwise movement means preferably comprise a resilient element rigidly connected to the housing and a knurled disc coupled to the second toothed wheel, and the means for disconnecting preferably comprise a cam disc which is rotatable by means of a control element.

Through the fact that according to the invention use is made of cheap, generally available toothed belts, the tube according to the invention can be made considerably more cheaply than the known tube, and the tube according to the invention, in particular as regards the disconnection of the means for permitting stepwise movement of the toothed belt, can be operated much more easily with one hand, because it need be turned only through a small angle relative to the housing along the housing wall, and does not have to be pulled out relative to the housing, as in the case of the known tube.

BRIEF SUMMARY OF THE DRAWINGS

Further advantages of the invention will become clear from the description which follows of an example of an embodiment with reference to the drawing. In the drawing.

DETAILED DESCRIPTION OF THE INVENTION

Figure 1:
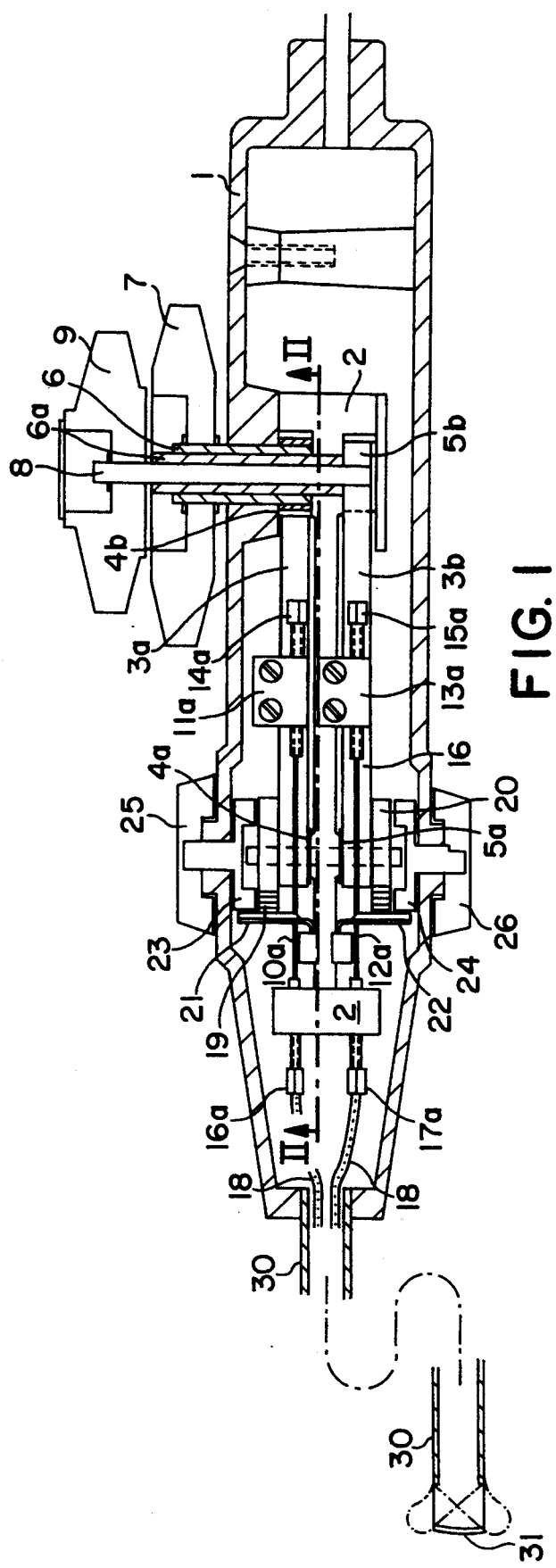
FIG. 1 shows a side view of a cross-section of the manipulator according to the invention.
Figure 2:
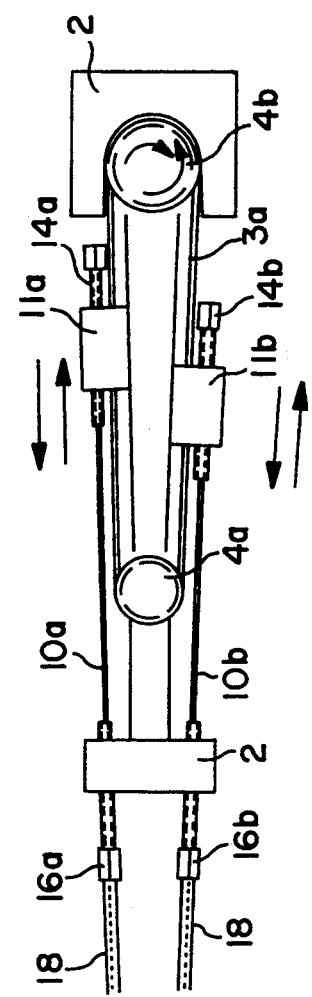
FIG. 2 shows a side view along the line II—II in FIG. 1 of only the movement mechanism for a pair of cables.

The manipulator of the tube 30 according to the invention, as shown in FIGS. 1 and 2, comprises a housing 1 which is round or rectangular in cross-section and is composed of two parts fixed to each other by, for example, screws. A frame 2 is rigidly fixed to the housing 1, for example by means of screws. The housing has fitted in it two toothed belts 3a and 3b. Toothed belt 3a is guided with the toothed side at one end over a toothed wheel 4a and at the other end over a toothed wheel 4b. In the same way the toothed belt 3b is guided over toothed wheels 5a and 5b. The toothed wheels 4a, 4b and 5a, 5b are rotatable mounted relative to the frame 2, and the toothed wheel 4b is further coupled by means of a hollow shaft 6 to a control knob 7. The toothed wheel 5b is connected by means of a shaft 8 running through a fixed sleeve 6a to a control knob 9. The shaft 6 is guided rotatable in a manner which is known per se through the housing 1 and the fixed sleeve 6a, and the shaft 8 is also rotatable in a manner which is known per se relative to shaft 6, so that the toothed wheels 4b and 5b, and thus the toothed belts 3a and 3b, can be rotated independently of each other by means of control knobs 7 and 9 respectively.

A first pair of control cables 10a and 10b is connected to the toothed belt 3a by means of connecting blocks 11a and 11b respectively. In the same way a second pair of control cables 12a and 12b (not shown in the figure) is connected to the toothed belt 3b by means of connecting blocks 13a and 13b respectively (not shown in the figure). The connecting blocks are made of, for example, two parts fixed to each other by means of screws, the part lying on the toothed side of the toothed belt at the side facing the toothing preferably also being provided with a corresponding toothing in order to ensure a correct positioning of the connecting block, while even in operation the connecting block cannot be pulled askew as a result of tensile forces exerted by the cables.

It is possible by means of the control cables 10a, b and 12a, b to move the flexible end 31 of the tube 30. The flexible end 31 of the tube 30 can be fixed in any desired position in the manner described below in connection with the knurled discs 19 and 20.

The control cables 10a, b and 12a, b are preferably fixed by their ends to elongated screwed sleeves 14a, b and 15a, b (15b not shown in the figure), which screwed sleeves are threaded on the outside and fitted rotatable in a corresponding screw thread formed in the connecting blocks. This design, which is already known per se in other types of equipment, has the advantage that the cables can be tensioned in a simple manner in order to be able to set the flexible end accurately. The control cables are preferably also guided via screwed sleeves 16a, b and 17a, b (17b not shown in the figure) through the frame 2, the screwed sleeves being rotatable relative to the frame. A sheath 18 of the control cables ends in the open ends of the screwed sleeves facing the front side of the housing, as a result of which a turning of the screwed sleeves 16a, b and 17a, b provides a further adjustment facility for the cables.

Knurled discs 19 and 20 are rigidly fixed to the toothed wheels 4a and 5a respectively. The free leg of respective L-shaped resilient elements 21 and 22 can be accommodated in the knurls of the knurled discs 19 and 20, the other leg in each case being rigidly fixed to the frame 2. Provision is also made for cam discs 23 and 24, which are rotatable mounted in the housing 1 and can be turned by knobs 25 and 26 respectively from a first position to a second position. The peripheries of the cam discs 23 and 24 lie near the ends of the free legs of the resilient elements 21 and 22 respectively. The cam discs are dimensioned in such a way that in the first position of the knobs 25 or 26 the periphery of the cam disc corresponding to said knob is clear of the resilient element, which can consequently fall into a notch of the corresponding knurled disc, so that when the knobs 7 and/or 9 are turned the toothed belts 3a and 3b, and thus the control cables, are moved stepwise due to the fact that the resilient elements always engage in a next notch of the knurled disc.

In the second position of the cam disc 23 or 24 it lies against the resilient element 21 or 22 and presses it away until it is outside the periphery of the knurled disc in question, as a result of which the cables can be moved continuously and, if desired, rapidly by turning the knobs 7 and/or 9, for example in order to take the flexible end of the endoscope quickly to the vicinity of the position in the body to be examined, following which turning the knob 25 and/or 26, which can easily be carried out with one finger of the hand holding the housing, makes it possible to change over to the stepwise movement of the toothed belts, to permit accurate seeking of the end position.

The continuous movement facility also serves to prevent the flexible end from remaining in a fixed curved position on withdrawal of the tube 30 from the body, something which could seriously damage the inside of the body orifice in question.

In the above a description is given of a tube according to the invention, without details being given concerning the design of the actual endoscope and the flexible end thereof, but these parts need no further explanation because they can have different designs which are well-known in professional circles. The endoscope can comprise, for example, an optical fibre which is guided through the housing 1, and of which the end comes out at the rear side of the housing, seen on the right in the figure, and is coupled to suitable optical elements to permit looking into the body through the fibre. Another possibility is that the flexible end of the endoscope contains an ultrasonic transducer and that the signal cable of said transducer is guided through the housing 1.

Finally, it is also pointed out that, although the example of an embodiment described has a manipulator with two pairs of control cables, the principle of the invention is also applicable without further ado if only movements in one plane need be carried out, for which a tube which is provided with a manipulator then has only one pair of control cables.

I claim:

1. A manipulator assembly for an endoscope, which comprises:
    a housing member;
    a first pair of control cables for said endoscope extending into said housing member;
    first and second gear members positioned for rotation within said housing member;
    an endless toothed belt member coursed about said first and second gear members, said control cables being mounted to said toothed belt member;
    control means coupled to said first gear member for rotating said first gear member;
    stepping means engaging said second gear member for effecting stepwise movement of said endless toothed belt member; and
    control element means disposed outside said housing for disengaging said stepping means.

2. The manipulator assembly as defined in claim 1 and further including a second pair of control cables extending into said housing member connected to a second endless toothed belt member coursed about similarly provided with first and second gear members positioned within said housing and similarly provided with control means, stepping means and control element means.

3. The manipulator assembly as defined in claim 2 wherein each of said stepping means is a resilient element connected to said housing to engage a knurled disc coupled to said second gear member and wherein each of said control element means includes a cam disc rotatably positioned by a control member for disengaging said resilient element from said knurled disc.

4. The manipulator assembly as defined in claim 2 wherein said first and second pair of control cables are connected by block members to said first and second endless toothed belt members respectively, each of said block members being provided with teeth corresponding to teeth of said respective endless toothed belt member.

5. The manipulator assembly as defined in claim 4 wherein said first and second pair of control cables are adjustably mounted to said respective block members by sleeve members threadably disposed within said block members.

6. The manipulator assembly as defined in claim 1 or 2, wherein said stepping means is a resilient element connected to said housing to engage a knurled disc coupled to said second gear member and wherein said control element means includes a cam disc rotatably positioned by a control member for disengaging said resilient element from said knurled disc.

7. The manipulator assembly as defined in claim 1 or 2 wherein said first pair of control cables are connected by block members to said endless toothed belt member, each of said block members being provided with teeth corresponding to teeth of said endless toothed belt member.

8. The manipulator assembly as defined in claim 7 wherein said first pair of control cables are adjustably mounted to respective block members by sleeve members threadably disposed within said block members.

* * * * *